(12) United States Patent
Barongan (10) Patent No.: US 10,117,645 B2
(45) Date of Patent: Nov. 6, 2018

(54) APPARATUS FOR REMOVING DEVICES IMPLANTED IN THE BODY

(71) Applicant: Mark Barongan, San Diego, CA (US)

(72) Inventor: Mark Barongan, San Diego, CA (US)

( * ) Notice: Subject to any disclaimer, the term of this patent is extended or adjusted under 35 U.S.C. 154(b) by 55 days.

(21) Appl. No.: 13/770,489

(22) Filed: Feb. 19, 2013

(65) Prior Publication Data

US 2014/0236162 A1    Aug. 21, 2014

(51) Int. Cl.
*A61B 17/58* (2006.01)
*A61B 17/60* (2006.01)
*A61F 2/00* (2006.01)
*A61B 17/00* (2006.01)
*A61B 17/50* (2006.01)
*A61B 17/02* (2006.01)
*A61B 17/28* (2006.01)

(52) U.S. Cl.
CPC .............. *A61B 17/00* (2013.01); *A61B 17/50* (2013.01); *A61B 17/02* (2013.01); *A61B 2017/2837* (2013.01)

(58) Field of Classification Search
CPC ............ A61B 17/50; A61B 2017/2945; A61B 2017/2947; A61B 17/28; A61B 17/2812; A61B 17/2816; A61B 17/282; A61B 17/2841; A61B 17/29; A61F 2/4611; A61F 2/4603
USPC ......... 606/99, 90, 91, 86 A, 86 B; 623/22.12
See application file for complete search history.

(56) References Cited

U.S. PATENT DOCUMENTS

| 2,994,321 A | * | 8/1961 | Tischler | A61B 10/02 600/564 |
| 6,206,896 B1 | * | 3/2001 | Howell | A61B 17/122 606/151 |
| 7,087,070 B2 | * | 8/2006 | Flipo | A61B 10/06 606/205 |
| 2014/0107658 A1 | * | 4/2014 | Yaremchuk | A61B 17/282 606/99 |

* cited by examiner

*Primary Examiner* — Si Ming Ku (57) ABSTRACT

An apparatus for displacing an implant, such as a pacemaker or ICD generator or loop recorder, which can be used during surgical procedures to facilitates manipulation of the implanted device. The apparatus can be used to apply force to the implant in order for the operator to tug to loosen the implanted device without causing unnecessary movement or dislodgement of implanted leads that are connected to the implanted device. The apparatus can have features of various shapes and sizes depending on the size of the patient as well as size and shape of the implanted device.

10 Claims, 9 Drawing Sheets

APPARATUS FOR REMOVING DEVICES IMPLANTED IN THE BODY

FIELD OF INVENTION

The present invention is related to an apparatus for enabling the extraction of an implant, such as an implanted device from the body while minimizing excessive cutting of the skin or cavity pocket.

BACKGROUND OF THE INVENTION

Implantable devices, such as a pacemaker ICD generator or a loop recorder, are often implanted into the human body to aid specific biological functions. When the device has served its usefulness, doctors often need to perform surgical procedures to remove the implanted device. Under certain circumstances, doctors may remove and replace parts of the implanted device, such as a battery, or components of artificial hips, artificial knees, spinal prosthetics, or components used in traumatic fracture repair, or tunneling tools and their accessories, rather than removing the implanted device itself.

Typically, when an implanted device is being removed, such as when a pacemaker generator is being removed, the general area where the implanted device is located is prepared with anesthetics. An incision is made in the skin and tissues and scar tissues around the device are resected. Sutures anchoring silicone covered leads or wires attached to the implanted device or anchoring the device itself are cut. Typically, these leads and wires are sutured into the bottom aspect of the open pocket, typically to the bottom side/inner edge of the pocket using the wire suture tabs sleeves, which wrap around the leads or wires. Sutures are generally not cut from the wire suture tab sleeves. Wires are only removed when there is a lead or wire fracture, or the lead or wire is infected, or when there is a manufacture recall on the product and the product needed to be explanted.

Once the device or generator is loosened from the scar tissue and is ready to be taken out, the clinician will need a tool to extract the generator or battery from the pocket.

Methods presently available generally involve the use of multiple surgical tools. A conventional method for extracting an implanted device is to cut the skin and fillet the skin to create a pocket to see the exact location of the implanted device. Once the pocket is opened, it is often kept open with a retractor such as a Weitlaner Retractor or equivalent. Doctors often have to over stretch the opening pocket in order to allow other tools, such as a sponge forceps, curved Kelley, or curved, straight or angled hemostats, or skin retractor to be inserted and used to extract the implanted device out of its implanted cavity.

There are several drawbacks associated with the conventional method. First, the opening pockets are stretched out unnecessarily to create an opening sufficient wide for the surgeon to see and pinpoint the exact location of the implanted device and for insertion of multiple surgical tools for extraction. Sutures that may or may not anchor the device to the opening pocket are cut in attempts to free the device. A Weatlander retractor stretches the pocket or cavity where the generator is recessed in. Once the pocket is held open by the Weatlander retractor, a sponge forceps, curved Kelley, hemostat or skin retractor is used to try and excavate the generator out of the pocket or cavity. Many attempts are made to explant the generator that has surrounding scar tissue. Often, numerous attempts are made to grab the implanted device, with curved Kelleys, sponge forceps, hemostat or skin retractor and other surgical apparatus, causing the implanted device's casing to become marred, sometimes damaged. Furthermore, some of the apparatus used to extricate the device have raised edges or teeth. Those teeth can scrape small parts of metal into the tissue pocket from where the device is being extricated.

The tugging and manipulation of the implanted device to extract it from the body can also cause movement or dislodgment of implanted leads in the body or heart that are connected to the implanted device. This can increase the overall cost of a simple procedure, such as a generator replacement procedure, and compromise the safety of the patient. The cost can increase from a simple generator change to a dual lead revision and generator replacement.

Accordingly, it is desirable to provide an improved apparatus and method that overcome drawbacks and inadequacies of known devices and methods.

SUMMARY OF THE INVENTIONS

An implant extracting apparatus generally can include two handles connected to two jaw portions through a connecting mechanism that can transfer force applied to the two handles to the jaw portions to create gripping force between the jaw portions. According to the invention, the implant extracting apparatus can include a first handle, a second handle, a first jaw portion having a tapered distal end, a second jaw portion; and a connecting mechanism, where in the connecting mechanism transfers a force applied to the first and second handles to the first and second jaw portions, creating a gripping force between the first and second jaw portions, and the gripping force is controlled by selectively altering the distance between the first and second handles.

Furthermore, according to the invention, an apparatus for removing an implant can include a first leg having a first proximal end on a first plane and a first distal end on a second plane different from the first plane, a second leg having a second proximal end on the first plane and a second distal end on the second plane, and a connecting mechanism connecting the first leg and second leg, constructed and arranged such that when the distance between the first and second proximal ends are selectively altered on the first plane, the distance between the first and second distal ends are correspondingly altered on the second plane. The apparatus' proximal ends can each comprise a handle and the distal ends can each comprise a jaw portion. The handles can be constructed and arranged within a selected distance from each other. In one embodiment, increasing the distance between the handles increases the distance between the jaw portions. Alternative, reducing the distance between the handles increases the distance between the jaw portions in another embodiment. The apparatus can also include a bolt. The displacement of the bolt can alter the distance between the two proximal ends. Alternatively, the apparatus can include a spring.

BRIEF DESCRIPTION OF THE DRAWINGS

For a fuller understanding of the invention, reference is made to the following description taken in connection with the accompanying drawings, in which.

DETAILED DESCRIPTION OF THE PREFERRED EMBODIMENTS

Certain exemplary embodiments of the present invention will now be described with reference to the drawings. In general, such embodiments relate to an apparatus or a method of extracting an implanted device. Whereas reference is made to removing an implanted device, it is to be understood that any displacement, including insertion, adjustment and removal of any object, regardless of size, shape or construction, is within the scope of the invention.

Figure 1:
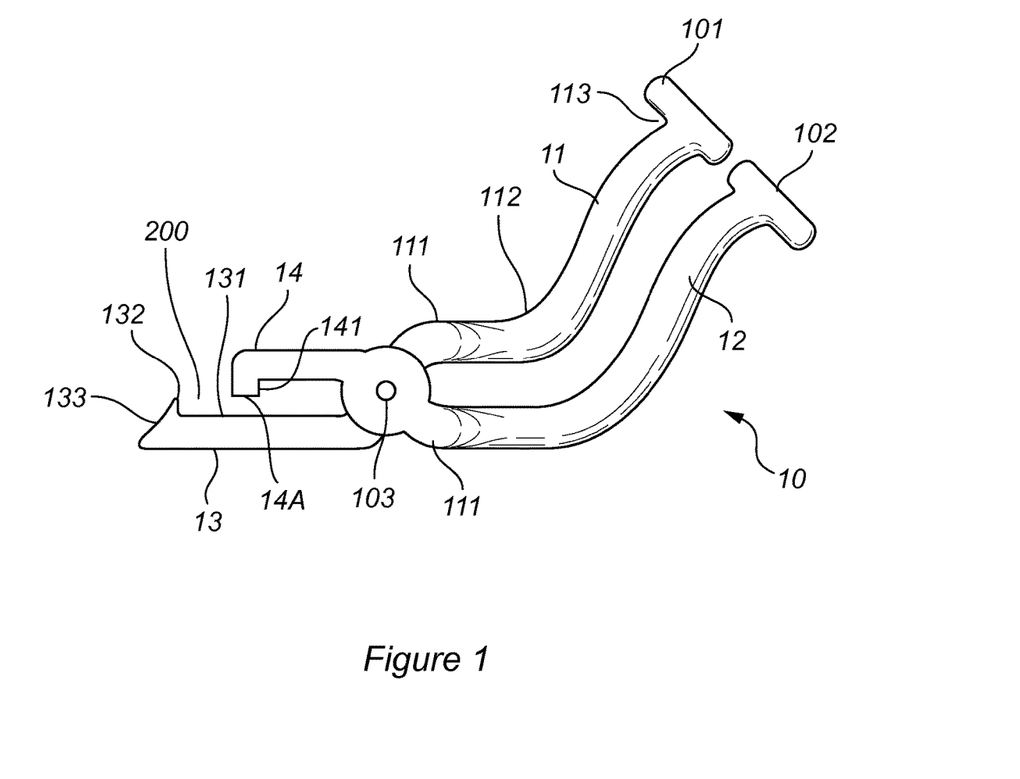
FIG. 1 is a side view of an implant extraction apparatus in accordance with an embodiment of the present invention.

A first embodiment of an implant-extracting apparatus is shown in FIG. 1 and will be described herein. The implant extracting apparatus 10 includes two elongated legs, a first leg 101 and a second leg 102. Each leg has a jaw portion in the distal end and a handle in the proximal end. The first handle 11 is at the proximal end of the first leg 101, which also has a first jaw portion 13 at its distal end. Similarly, the second handle 12 is at the proximal end of the second leg 102, which also has a second jaw portion 14. The first handle 11 can control the movement of the first jaw 13, while the second handle 12 can control the movement of the second jaw 14, wherein the jaws 13, 14 define a receiving area 200 for receiving an implanted device. Handles 11 and 12 can reside on the same plane as jaws 13 and 14. Alternatively handles 11 and 12 can reside on a first plane while jaws 13 and 14 reside on a second plane.

A connecting mechanism 103 joins the two legs 101, 102 and allows the jaw portions 13, 14 to move between an opened position and a closed position. Although the connecting mechanism 103 may serve as a fulcrum, pivotally connecting the legs 101, 102, as shown in FIG. 1, the legs 101, 102 may also be connected parallel to each other. In such a parallel arrangement, the legs may be squeezed and released to create a gripping force upon the jaw portions of the legs. Other arrangements of the legs can be provided in accordance with application specific design choice without deviating from the scope of the invention.

Figure 4:
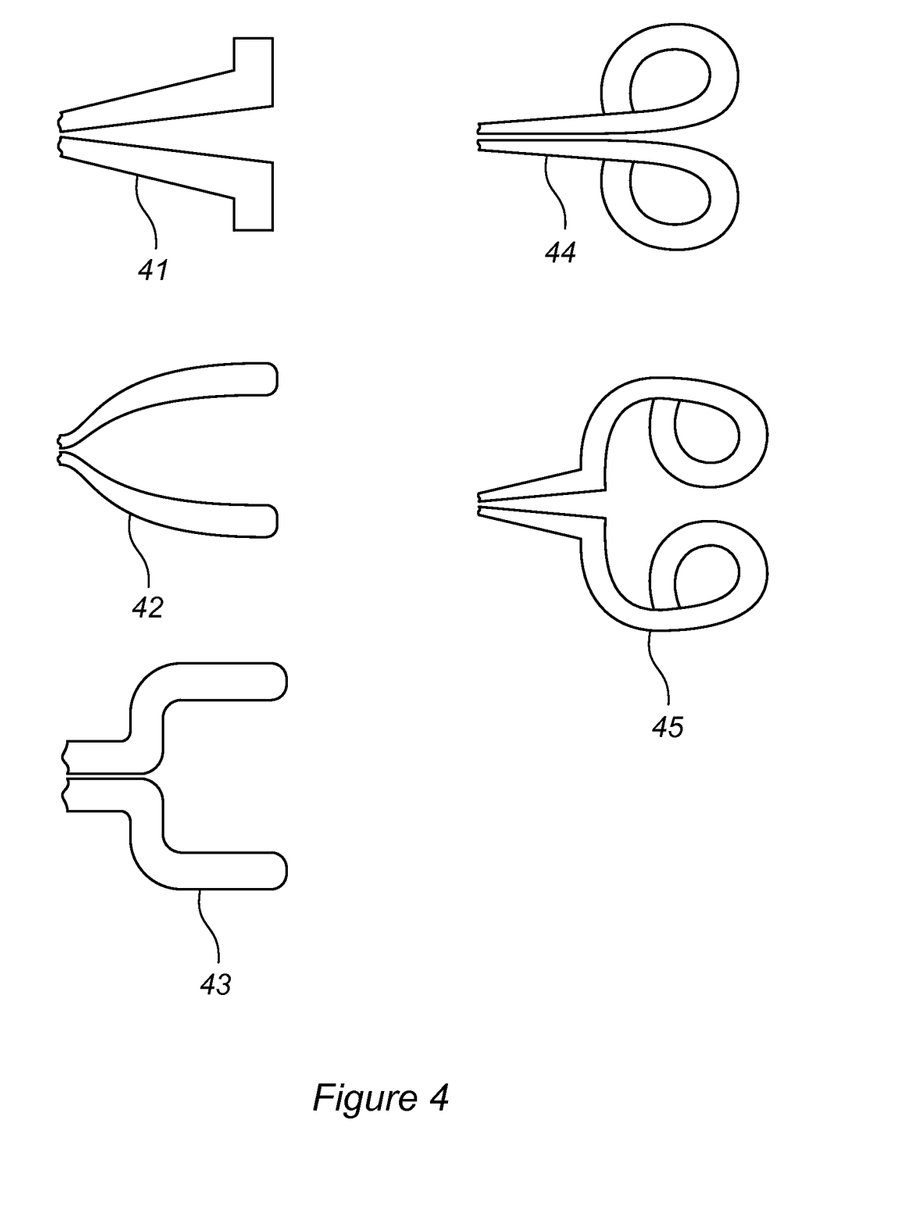
FIG. 4 shows various shapes of the handles.
Figure 5:
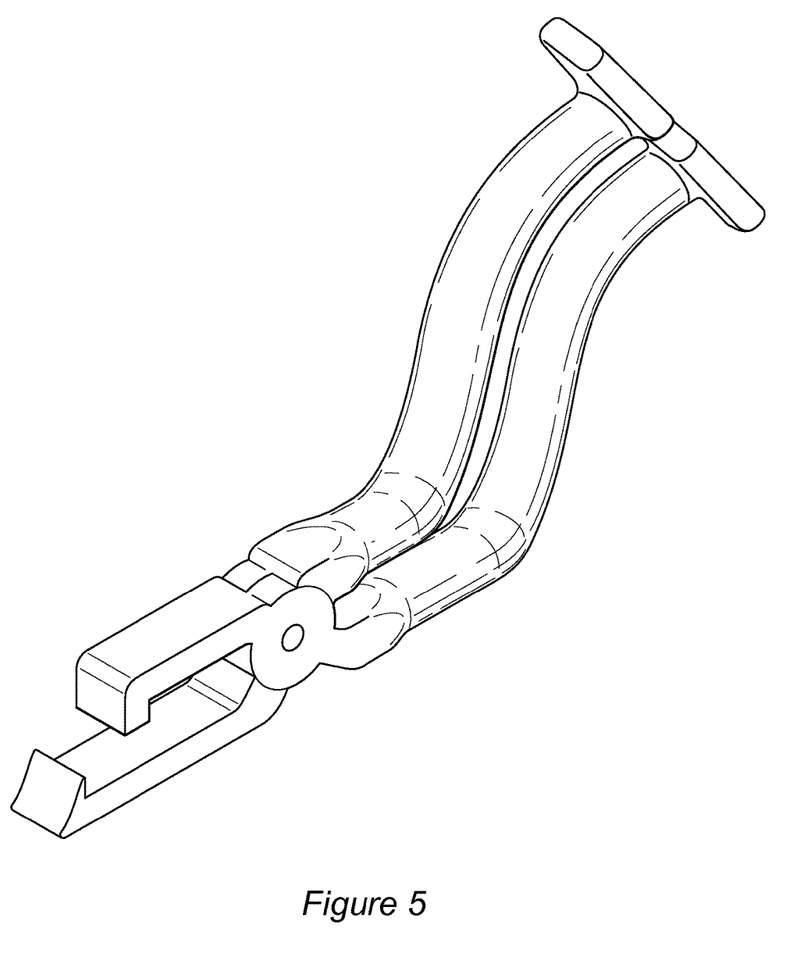
FIG. 5 is a three-quarter perspective of an implant extraction apparatus in accordance with an embodiment of the present invention.

The first and second handles 11 and 12 preferably are ergonomically designed. They can have optional curvatures 111, 112, 113 that may allow the operator to get a better grip to manipulate the apparatus and extricate the implanted device. For example, the ergonomic curve 112 on the first leg 101 can support the pinky finger and the curve 112 on the second leg 102 can support the adjacent bottom palm edge, which can provide a comfortable grip when the first handle 11 and second handle 12 are squeezed together simultaneously. The curve 113 on the first leg 101 can sit on the upper edge of the index finger's second joint and curve 113 on the second leg 102 can sit on or above the webbing or crux of the hand where the thumb and index finger meet. The shape of handles 11 and 12 can be angled, curved, straight or any other shape according to application design choice. FIG. 4 illustrates non-limiting examples of handles 41, 42, 43, 44, and 45.

The first jaw portion 13 preferably has a tapered end 133, with decreasing thickness toward the distal end. The tapering 133 may better facilitate sliding and leading the first jaw portion 13 into the skin or device pocket, and/or tunneling the first jaw portion 13 under or around the implanted device in, out or through the derma to reach an optimal position for extraction. The first jaw portion 13 may also be tapered along its width or depth or be in any shape that is suitable for facilitating insertion and manipulation in, out or through the derma and/or cavity of the body or the device pocket.

Figure 9:
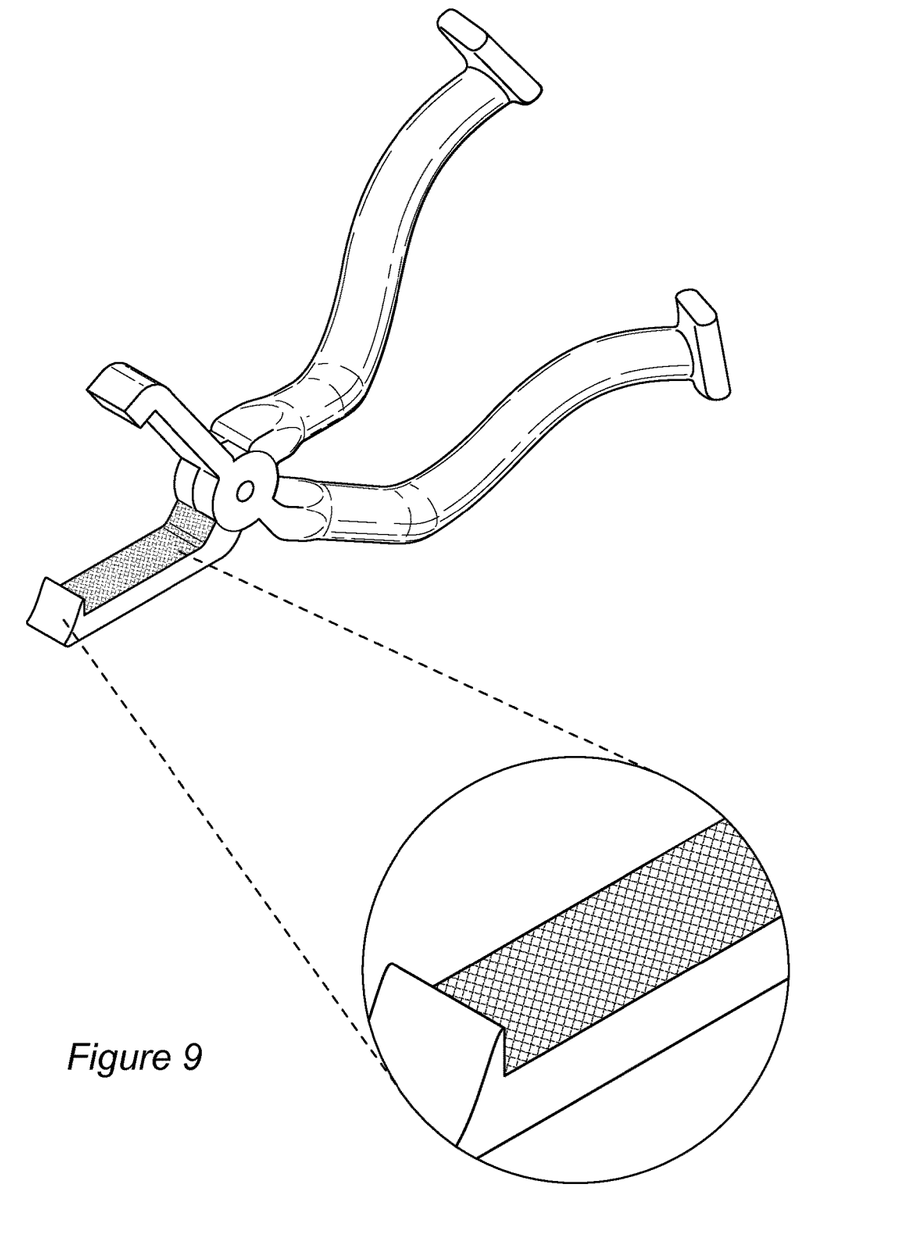
FIG. 9 is an exploded view of the jaw portion of an embodiment of the present invention, illustrating surface texture.

In the embodiment shown, the first jaw portion 13 has an elongated body, providing a surface 131 upon which the implanted device can rest. The surface 131 may include an anti-slip surface to prevent slipping when the apparatus is being used to displace an implanted device. The anti-slip surface can have textures, such as rough, raised, grooved, score lines, ridges and/or raised teeth surfaces. See FIG. 9.

Figure 2:
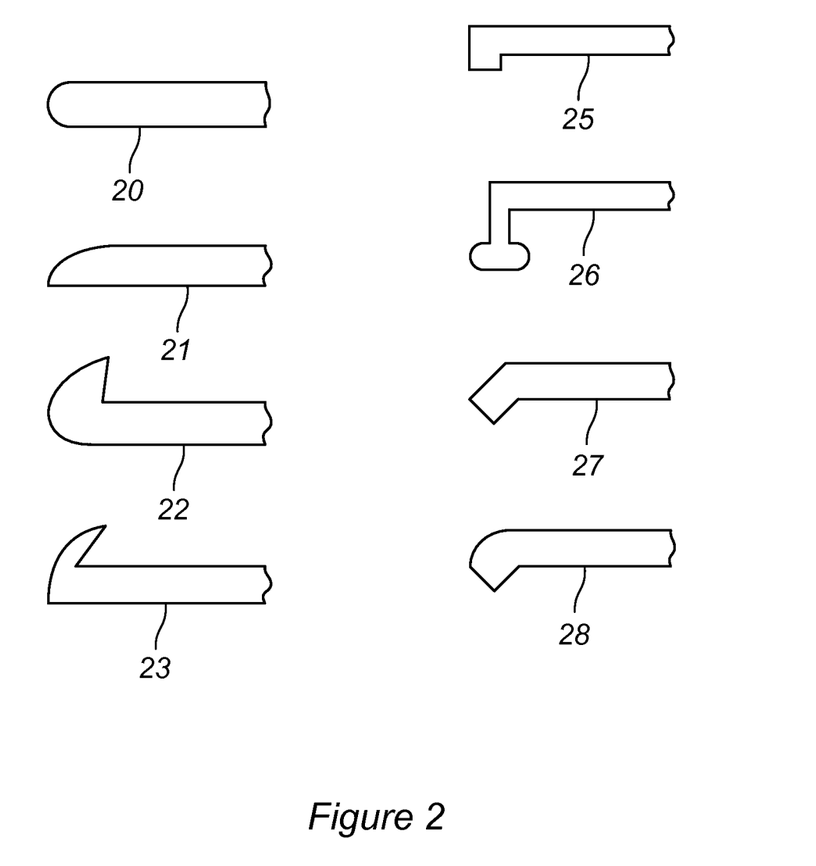
FIG. 2 shows various shapes of the jaw portions.

The first jaw portion 13 may also have a raised edge 132 defining the distal end of the surface 131, the raised edge 132 preferably protruding toward the second jaw portion 14. The shape of the raised edge 132 can be angled, curved, straight or any other shape according to application design choice. FIG. 2 illustrates non-limiting examples of raised edge 20, 21, 22, 23. The raised edge 132 is preferably constructed and arranged such that if the implanted device moves toward the distal end of the apparatus 10, the raised edge 132 can abut the implanted device, thus preventing the implanted device from being displaced out of the receiving area 200 between jaw portions 13, 14, for example, during extraction. If the length of the implanted device to be removed is less than the length of the surface 131, the device may rest on the surface 131 within the length of the surface 131. If the length of the implanted device is greater than the length of the surface 131, then a portion of the implanted device may rest on top of the raised edge 132 and the implanted device may extend beyond the receiving area 200.

The second jaw portion 14, preferably coordinating with the first jaw portion 13, may provide a gripping force to hold the implanted device in place during displacement, such as removal. It may have a tapered distal end, being tapered along its length, width and/or depth. The second jaw 14 may contain a gripping surface 141 that can vary in size or shape. The gripping surface 141 may have anti-slipping features, such as rough, raised, grooved, score lines, ridges and/or raised teeth surface. A textured surface 141 may prevent slipping when clamping onto a device.

The second jaw portion 14 preferably includes a protrusion 14A extending toward the first jaw portion 13, wherein the protrusion 14A defines the distal end of the gripping surface 141. The protrusion 14A is preferably constructed and arranged such that that if the implanted device moves toward the distal end of the apparatus 10, the protrusion 14A can abut the implanted device, thus preventing the implanted device from being displaced out of the receiving area 200. FIG. 2 illustrates non-limiting examples of the protrusion 25, 26, 27, 28. The protrusion 14A preferably also includes anti-slipping features. In the embodiment shown in FIG. 1, the second jaw portion 14 is shorter than the first jaw portion 13, such that an implanted device having a length equal to or less than the length of the surface 141 of the second jaw portion 14 may be received between the connecting mechanism 103 and the protrusion 14A. If the implanted device has a length greater than the length of the surface 141 of the second jaw portion 14, the protrusion 14A may apply a clamping force onto the implanted device toward the first jaw portion 13. Both the shape and the surface areas of first and second jaw portions 13, 14 can be specifically made to fit and extract specific implanted devices. The devices may include, but are not limited to, wires, generators, batteries, and the like.

The embodiment of the apparatus 10 illustrated has an opened position and a closed position. When the first handle 11 and second handle 12 are drawn apart, the first jaw portion 13 and the second jaw portion 14 are also drawn apart and the apparatus 10 is in the opened position. The width of the opening between the first jaw portion 13 and the second jaw portion 14 depends on the distance between the first handle 11 and the second handle 12. When the handles 11 and 12 are squeezed together, the jaws 13 and 14 move closer together in a clamp like manner. When the apparatus is in this closed position, the first and second jaw portions 13 and 14 together form a gripping mechanism, with the second jaw portion 14 biting down on the implanted device while the first jaw 13 holds the device in place.

The first and second jaw portions 13 and 14 can be fitted together in a predetermined manner so that when the two are in the closed position, the first jaw portion 13 provides adequate spacing for the implanted device, while the second jaw portion 14 provides adequate force to grip the implanted device, allowing the handler to hold on to and manipulate the implanted device in, within, or out of the implanted cavity. This can allow the clinicians to apply and transfer the gripping and/or torqueing force from the handles to the jaws efficiently, and to conduct a quick and exact extraction of the implanted device, avoiding unnecessary movement or dislodgment of implanted leads.

Figure 8:
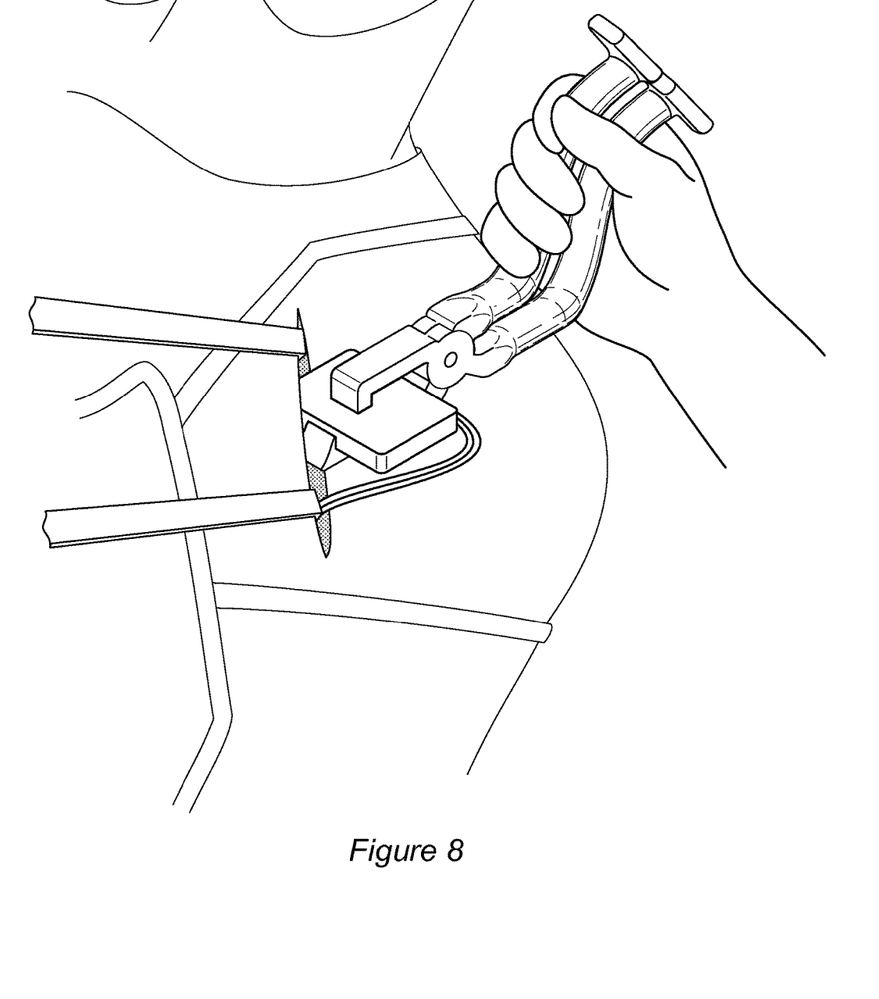
FIG. 8 illustrates the extraction of a generator using an embodiment of the present invention.

Extraction of the implanted device through the skin surface can be performed by widening the gap between the first jaw portion 13 and the second jaw portion 14. The operator can control and manipulate the first handle 101 while the apparatus 10 is in the opened position, to cause the first jaw portion 13 to tunnel and wedge into the device pocket under the object desired for removal. Once the first jaw 13 is in the proper position, with the implanted device resting within the receiving area 200, the operator can then squeeze the handles 11 and 12 together to close the jaw portions 13 and 14. The jaw portions 13 and 14 together can clamp onto the device, gripping the device. The operator can maneuver the handles 11, 12 to apply torqueing and/or pulling forces until the implanted device is free from the pocket without excessive tugging and over-cutting of the pocket opening. See FIG. 8.

The present invention preferably allows the implanted device to be grabbed and facilitates the extrication of the device, allowing for minimal tugging and dislodging of the leads. Furthermore, certain embodiments of the present invention can be used to assist in the insertion or positioning of an implantable device, for example, where resistance is met upon attempting to place a device into the skin pocket. In one embodiment, when a patient is of small stature and/or the patient does not want a large scar, the clinician can attach the implantable device's leads onto the implantable device and use an embodiment of the present invention to insert the device into the small pocket. The clinician may also grasp and hold the present invention with one hand and use the other hand to support the pocket opening to insure proper fitting and seating of the device in the pocket. A device constructed in accordance with the invention may help wedge the device in smaller pockets without excessive cutting of skins and tissues. The same approach may be used when the clinician's hand digits are larger than the pocket opening.

Figure 3:
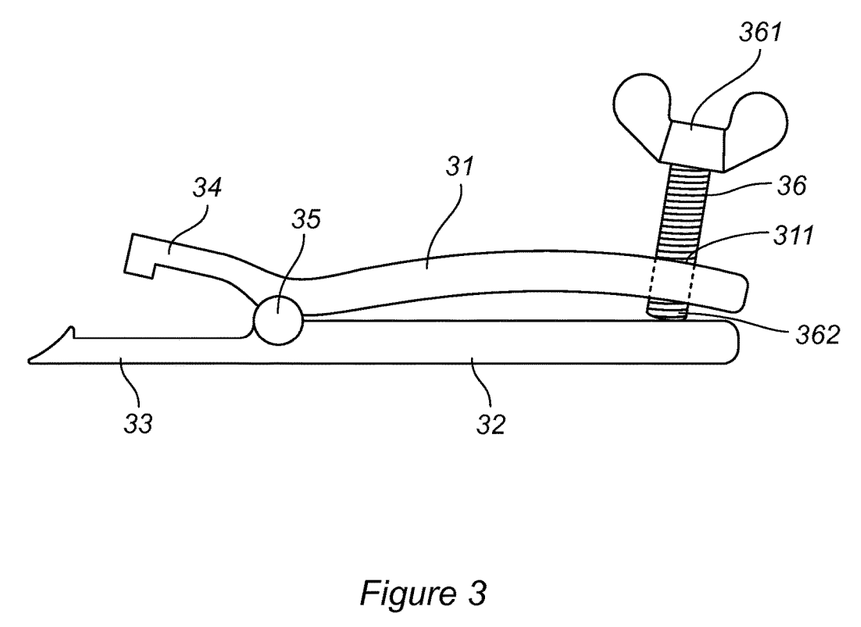
FIG. 3 is a side view of a second implant extraction apparatus in accordance with an embodiment of present invention.
Figure 6:
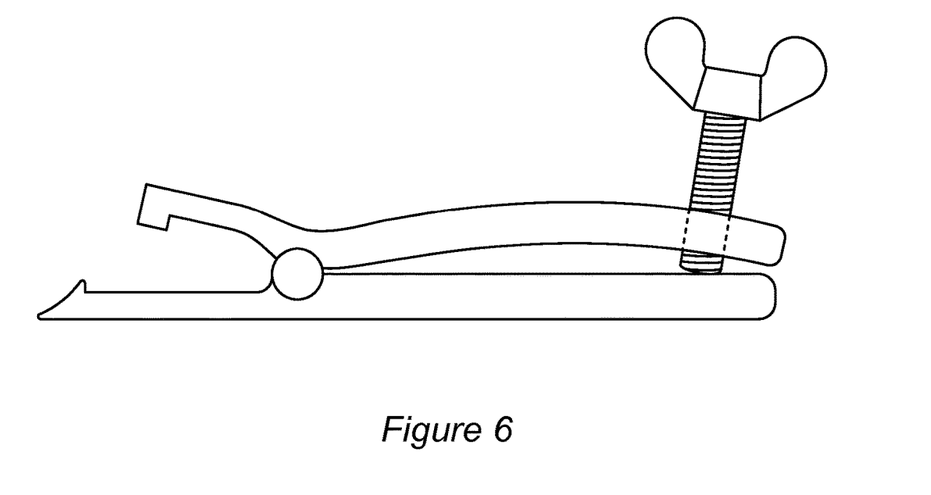
FIG. 6 illustrates the embodiment of FIG. 3 at an opened position.
Figure 7:
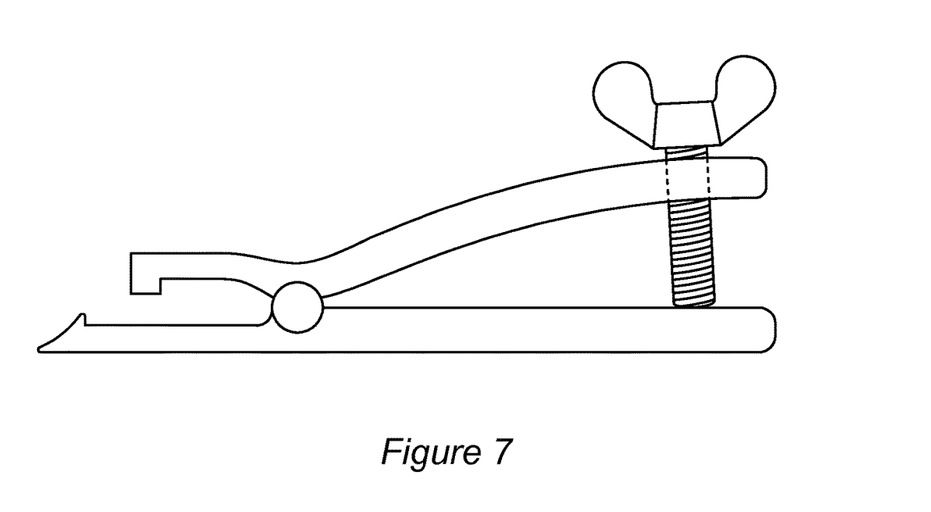
FIG. 7 illustrates the embodiment of FIG. 3 at a closed position.

Another embodiment of the invention is shown in FIG. 3. The apparatus as shown has handles 31, 32, jaw portions 33, 34, a connecting mechanism 35, and a screw 36. As shown, the screw 36 has a head 361 and a threaded body 362. The threaded body 362 is inserted into the handle 31 through a threaded receiver 311, constructed and arranged to receive the threading of the threaded body 362. When the head 361 of the screw-like screw 36 is rotated clockwise, the distance between handles 31 and 32 is increased, moving the apparatus's jaw an opened position to a closed position. See FIGS. 6 and 7. Accordingly, the jaw portion 33 and the jaw portion 34 can be moved closer to each other clamping down on the object, if any, positioned between jaw portions 33 and 34. When the head 361 is rotated counter-clockwise, the jaw portions 33, 34 will separate. In this embodiment, force is applied indirectly to the jaws to grip the implanted device by applying force onto the screw 36, which force is then transferred to the handles 31, 32, then to the jaw portions 33, 34, whereby the connecting mechanism 35 serves as a fulcrum, providing a pivot point. Whereas a threaded screw 36 is illustrated and described herein, it is to be understood that a bolt having a smooth surface, grooves, protrusions, and/or other adjustment mechanisms for adjusting the position of the bolt within handle 31, are contemplated without deviating from the scope of the invention. Likewise, handle 31 may include a receiving mechanism complementing such adjustment mechanism of the bolt, instead of the threaded receiver 311. FIG. 6 illustrates non-limiting examples of raised edge 20, 21, 22, 23.

Figure 10:
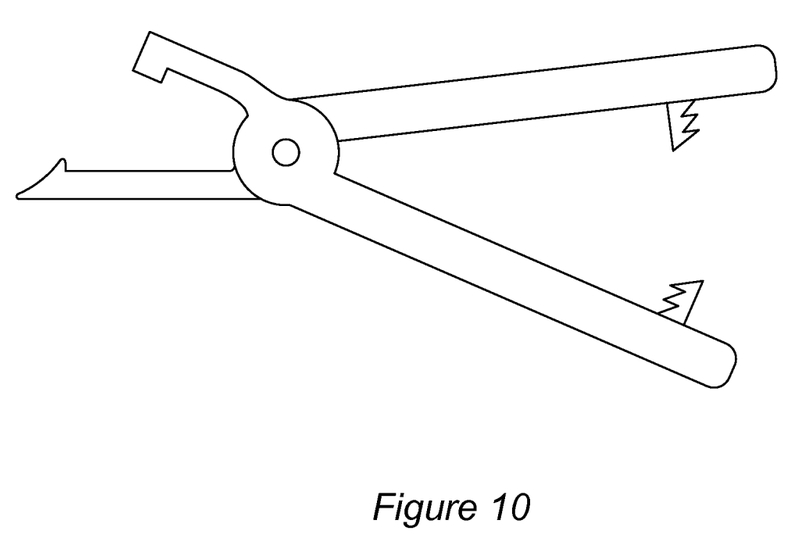
FIG. 10 illustrates an embodiment with handles with complementing lock-steps.

In another embodiment of the invention, the opening and closing of the jaw portions can be accomplished either applying direct pressure to the handles, or applying direct or indirect pressure through the use of screws, springs or other mechanisms. For example, the handles may have complementing lock-steps, see FIG. 10, on the handles. When pressure is applied to move the handles closer to each other, the lock-steps can lock with each other, preventing the handles from moving away from each other without the clinician having to apply continuous squeezing pressure onto the handles.

In addition, the movement of the handles can alter the distance between the jaw portions reciprocally or inversely. For example, in one embodiment, squeezing the handles toward each other can cause the jaw portions to move toward each other, thus applying a gripping force on a device positioned therebetween. In another embodiment, pulling the handles apart can cause the jaw portions to move toward each other, thus applying a gripping force on a device positioned therebetween.

The design of the retracting apparatus shown may reduce excessive tugging and difficulty in pulling an implanted device currently performed by alternative tools not meant for generator or implanted device extractions.

The examples provided are merely exemplary, as a matter of application specific to design choice, and should not be construed to limit the scope of the invention in any way.

Thus, while there have been shown, described and pointed out novel features of the present invention as applied to preferred embodiments thereof, it will be understood that various omissions and substitutions and changes in the form and details of the disclosed invention may be made by those skilled in the art without departing from the spirit of the invention. For example, the length of the legs, the angle between of the jaw portion and its respective handle portion, the shape of the curves on the handles, etc. can be changed without deviating from the scope of the invention as a matter of application specific to design choice. By way of non-limiting example, the handles may have hooks, loops, or other mechanisms for keeping finger(s) or hand in place while opening and closing the extraction apparatus. For example, the handles may have loops such as the handles of scissors or the handles may be U-shaped, which may facilitate the opening of the apparatus without releasing the apparatus. Alternatively, the jaw portions may be curved to facilitate receiving rounded devices therein, or have a specific shape to receive a specific device. Whereas the first jaw portion 13 is illustrated as being longer than the second jaw portion 14, it is contemplated that the jaw portions can be of equal length, or the second jaw portion 14 may be longer than the first jaw portion without deviating from the scope of the invention. Moreover, the jaw portions 13, 14, may have more than one raised edge 132 or protrusion 14A, respectively, protruding at either the same or varying height from the respective jaw portion 13, 14. Additionally, other alterations can be made, as a way of non-limiting example, the thickness, width, or shape of the legs may vary along the length of the legs as a matter of application specific to design choice, without deviating from the scope of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall therebetween.

What is claimed is:

1. An apparatus for displacing an implant, said apparatus comprising:
    a first piece having a first curved handle and a first jaw having a beveled distal end, the first curved handle having: a first connector parallel to the first jaw, a first grip positioned at an obtuse angle from the first connector and a first curve positioned between the first connector and the first grip;
    a second piece having a second curved handle and a second jaw, the second jaw being shorter than the first jaw,
    the second curved handle having: a second connector, a second grip positioned at an obtuse angle from the second connector and a second curve positioned between the second connector and the second grip; and
    a connecting mechanism pivotally connecting the first piece to the second piece, wherein the connecting mechanism is located between the first curved handle and the first jaw and between the second curved handle and the second jaw;
    wherein displacing the first curved handle toward the second curved handle creates a gripping force between the first jaw and the second jaw;
    wherein the first jaw comprises a flat inner surface and a raised edge proximate the beveled distal end, the raised edge extending toward the second jaw designed to receive an implant between the connecting mechanism and the raised edge, such that the implant is prevented from being displaced distally past the raised edge,
    wherein the first jaw and the second jaw are asymmetrical in shape and length;
    wherein the first grip and the second grip are longer than the first connector and the second connector.

2. The apparatus of claim 1, wherein the second jaw includes one or more protrusions extending toward the first jaw, the one or more protrusions constructed to apply a pressure on the implant toward the flat inner surface of the first jaw when the apparatus is closed.

3. The apparatus of claim 1, wherein the second curved handle is configured to contact an operator's palm when the operator squeezes the first curved handle and the second curved handle toward each other.

4. The apparatus of claim 1, wherein the first curved handle further comprises a third curve configured to contact an operator's index finger.

5. The apparatus of claim 1, wherein the connecting mechanism serves as a fulcrum, providing pivoting movements to the handles and jaws.

6. The apparatus of claim 1, wherein the flat inner surface of the first jaw comprises an anti-slipping surface.

7. The apparatus of claim 1, wherein the second connector is parallel to the second jaw.

8. The apparatus of claim 1, wherein said first grip having a proximal end and an end bar at said proximal end.

9. The apparatus of claim 1, wherein the first curved handle is configured such that an operator's pinky finger rests on the first curved handle at the first curve.

10. The apparatus of claim 4, wherein the first curved handle is configured such that an operator's pinky finger rests on the first curved handle at the first curve.

* * * * *